United States Patent [19]
Kiencke et al.

[11] Patent Number: 5,513,907
[45] Date of Patent: May 7, 1996

[54] METHOD AND CIRCUIT CONFIGURATION FOR DETERMINING A FRICTIONAL VALUE

[75] Inventors: Uwe Kiencke, Regensburg; Armin Daiss, Karlsruhe; Gregor Probst, Landshut, all of Germany

[73] Assignee: Siemens Aktiengesellschaft, Munich, Germany

[21] Appl. No.: 264,001

[22] Filed: Jun. 22, 1994

[30] Foreign Application Priority Data

Jun. 22, 1993 [EP] European Pat. Off. .............. 93109953

[51] Int. Cl.⁶ ..................................................... B60T 8/32
[52] U.S. Cl. ..................... 303/150; 180/197; 188/181 A; 303/174; 303/166; 364/426.02
[58] Field of Search ............................ 303/91, 100, 102, 303/104, 105, 106, 107, 108, 109, 110, 111, 93, 103, 174, 150, 163, 165, 174, 166; 73/9; 180/197; 188/181 A, 181 C, 181 R; 364/426.01, 426.02, 426.03

[56] References Cited

U.S. PATENT DOCUMENTS 4,794,538  12/1988  Cao et al. .............................. 303/166

FOREIGN PATENT DOCUMENTS 0219023   4/1987   European Pat. Off. ..
0323066   7/1989   European Pat. Off. ..
0312096   12/1992  European Pat. Off. ..
3833211   4/1990   Germany .
8903780   5/1989   WIPO .

OTHER PUBLICATIONS

Research Disclosure, vol. 270, No. 072, Oct. 10, 1986, pp. 633–634 (Anonymous) "Estimation of Road Surface Coefficient of Friction".

Primary Examiner—Douglas C. Butler
Attorney, Agent, or Firm—Herbert L. Lerner; Laurence A. Greenberg

[57] ABSTRACT

A frictional value between a motor vehicle tire and a road surface is determined for use in an ABS system or a traction control system. Various sensors at the automobile ascertain the vehicle speed and the brake pressure at individual wheels. The angular acceleration of the wheel is calculated from the angular velocity thereof. A wheel slip is calculated from the vehicle speed and from the angular acceleration. The dependency of the coefficient of friction is approximated from the wheel slip with a non-linear approximation equation. The current estimation value for the coefficient of friction is estimated with a recursive estimation algorithm from measurement values previously ascertained during a preceding measuring instant.

12 Claims, 4 Drawing Sheets

METHOD AND CIRCUIT CONFIGURATION FOR DETERMINING A FRICTIONAL VALUE

BACKGROUND OF THE INVENTION

FIELD OF THE INVENTION

The invention relates to a method and circuit configuration for determining a frictional value between a motor vehicle wheel and a road surface, wherein the vehicle speed, the angular acceleration of a wheel and a braking pressure are ascertained, a wheel slip is determined therefrom, and a frictional value is determined therefrom with an estimation algorithm. The method and the corresponding circuit serve to ascertain the current value of friction between a motor vehicle tire and the surface of a road. If this current frictional value is known accurately, then anti-lock brake systems (ABS) can be regulated especially precisely. For systems that provide traction control, anti-slip, four-wheel steering, driver information, and rough road detection as well, accurate knowledge of the dynamic friction can be useful.

A system for ascertaining the road adhesion between a tire and a road surface has been heretofore known from European published patent specification 0 323 066 B1. Sensors detect a road wheel turn angle, a steering force, and a vehicle speed. A processor processes the three sensor signals, and reads a coefficient of friction from a table, i.e. a road adhesion of the tire, associated with the three signals. Measuring the steering force is quite complicated. Moreover, the coefficient of friction also depends on other values besides the driving parameters measured by the three sensors.

In another prior art apparatus, as described in European published patent specification 0 312 096 B1, the coefficient of friction, which is dependent on the lateral acceleration dynamics of the vehicle, is calculated with a formula derived from force equilibrium at the wheels. To that end, the signals of sensors for lateral acceleration, steering angle of the front and rear wheels and vehicle speed, and the contents of a memory for stability factors such as the vehicle mass, the distances between the center of gravity and the front or rear axle, the curve forces on the front and rear wheels, and the yawing moment are evaluated. Once again, the effort and expense, especially for the sensors, are quite high and there is no provision for using the calculated coefficient of friction for anti-lock control.

SUMMARY OF THE INVENTION

It is accordingly an object of the invention to provide a method and a circuit configuration for determining a frictional value, which overcomes the hereinafore-mentioned disadvantages of the heretofore-known methods and devices of this general type of which makes it possible to determine a variable coefficient of friction between the vehicle tire and the road at little effort or expense and as accurately as possible. The thus determined frictional value should enable improved regulation of wheel braking and wheel slip.

With the foregoing and other objects in view there is provided, in accordance with the invention, a method for determining a frictional value between a motor vehicle tire and a road surface. The method comprises the steps of:

ascertaining values of vehicle speed, angular acceleration of a vehicle wheel, and brake pressure;

calculating a wheel slip from the values;

approximating a dependency of a coefficient of friction from the wheel slip with a non-linear approximation equation;

estimating a current estimation value for the coefficient of friction with a recursive estimation algorithm from measurement values previously ascertained during a preceding measuring instant; and determining a frictional value between a motor vehicle tire and a road surface from the coefficient of friction estimated with the recursive estimation algorithm.

In accordance with a further mode of the invention, the method further comprises approximating the coefficient of friction in the approximating step with the equation $$\mu(s) = As + B\sqrt{s} ,$$

wherein A and B are parameters for the approximation, $\mu$ is the coefficient of friction, and s is the wheel slip.

In accordance with another mode of the invention, the method further comprises approximating the coefficient of friction in the approximating step with the equation $$\mu(s) = \frac{s}{A + Bs + Cs^2} ,$$

wherein A, B and C are parameters for the approximation.

In accordance with an added mode of the invention, the method further comprises estimating the coefficient of friction $\mu$ with the following recursive estimation algorithm:

$$\hat{\mu}(n) = \hat{\mu}(n-1) + k(n)(y(n) - X^*\hat{\mu}(n-1)),$$

in which $$y(n) = \frac{\omega_R(n) - \omega_R(n-1)}{T_A} + \frac{\mu_B A_B r_B}{\Theta_R} p_B(n)$$

is a variable formed from the measured values, $\omega_R$ is an angular speed of the respective wheel, and n is a dummy index of consecutive measurement instants;

$$X = \frac{m_A g r_R}{\Theta_R}$$

is a vehicle parameter, $m_A$ is a portion of a vehicle mass on the respective wheel, $r_R$ is a rolling radius of the wheel, and $\Theta_R$ is a mass moment of inertia of the wheel;

$$k(n) = \frac{1}{1 + X^2 P(n-1)} X * P(n-1)$$

is an amplification factor for error feedback; and $P(n-1) = 10^{q*}(y(n-1) - X^*\hat{\mu}(n-1))^2$ is a covariance of an estimation error at a measurement instant n-1;

In accordance with yet another mode feature of the invention, the method further comprises determining the coefficient of friction as a function of a wheel slip with a recursive estimation algorithm.

In accordance with again another mode of the invention, the method further comprises determining the coefficient of friction on the basis of a model $$\mu(s) = As + B\sqrt{s}$$

in which A and B are curve parameters with a vector representation $b^T = [AB]$ calculated from the measured wheel slip values with the vector representation $X^T = [s\sqrt{s}]$ and from a previously ascertained coefficient of friction μ(n−1), and determining a current coefficient of friction μ(n) with the following estimation algorithm:

$$\mu(n) = X^T(n) * \hat{b}(n),$$

in which $$\hat{b}(n) = b(n-1) + k(n-1)(\mu(n) - X^T(n)\hat{b}(n-1))$$

$$k(n) = P(n-1)X(n)(1 + X^T(n)P(n-1)X(n))^{-1}$$

$$P(n-1) = 10^{q*}|\mu(n-1) - X^T(n-1)\hat{b}(n-1)|^{2*}I$$

and I is a unit matrix.

Alternatively, the coefficient of friction μ(s) is determined on the basis of a model $$\mu(s) = \frac{s}{A + Bs + Cs^2}$$

wherein A, B, and C are parameters for the approximation, and s is the wheel slip.

In accordance with again an additional mode of the invention, the method further comprises transmitting the frictional value determined in the determining step to an anti-lock brake system or a traction control system.

With the above and other objects in view, there is also provided, in accordance with the invention, a circuit configuration for determining a coefficient of friction between a motor vehicle tire and a road surface, comprising: a plurality of sensors disposed at a motor vehicle for continuously measuring an angular speed of a wheel and a braking pressure at a wheel; an evaluation circuit connected to the sensors and receiving the signals from the sensors, the evaluation circuit including means for calculating an angular acceleration from the angular speed measured by a respective one of the sensors; and means for evaluating a coefficient of friction between a motor vehicle tire and a road surface from the angular acceleration and from the braking pressure with a recursive estimation algorithm.

In accordance with another feature of the invention, the circuit configuration further includes means for connecting an output of the evaluation circuit to an anti-lock brake system or to a traction control system.

In accordance with a concomitant feature of the invention, the system includes means for calculating a wheel slip from the vehicle travel speed and from the angular acceleration, and means for approximating a dependency of a coefficient of friction between a tire and a road surface from the wheel slip with a non-linear approximation equation.

The advantages of the invention include among others that the coefficient of friction is ascertained with time-tested, effective estimation algorithms, which here are embodied such that the effort and calculation and the storage capacity required are kept in bounds.

Other features which are considered as characteristic for the invention are set forth in the appended claims.

Although the invention is illustrated and described herein as embodied in a method and circuit configuration for determining a frictional value, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which:

DESCRIPTION OF THE PREFERRED EMBODIMENTS

Figure 1:
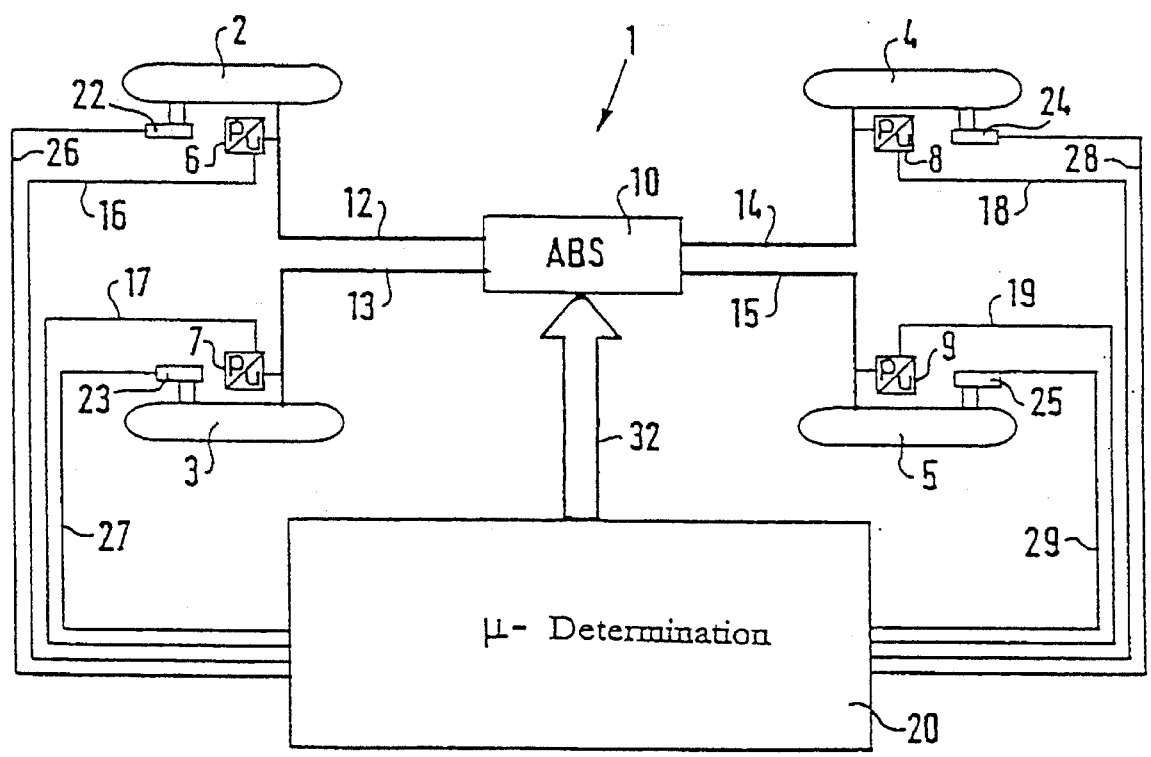
FIG. 1 is a schematic view of a motor vehicle with an anti-lock brake system (ABS) provided with a system for determining a frictional value according to the invention.

Referring now to the drawings and first, particularly, to FIG. 1 thereof, there is seen a schematic of a motor vehicle with an anti-lock brake system (ABS). The motor vehicle 1 has two front wheels 2 and 3 and two rear wheels 4 and 5. The wheels are provided with brake pressure sensors 6–9, which may, for instance, be disposed at the wheel brake cylinders, or at the brake lines. The sensors 6–9 are supplied with regulated pressure from the hydraulic block 10 of an anti-lock control unit (ABS) via hydraulic lines 12–15.

The brake pressure sensors 6–9 convert a brake pressure p prevailing at the applicable wheel into an electrical voltage signal u. The voltage signals u for each wheel pass over signal lines 16–19 to reach an electronic evaluation circuit 20, where they are evaluated in a manner to be described hereafter. The evaluation circuit 20 is a component of an anti-lock brake system control unit—not separately illustrated—that separately regulates the brake pressure for the individual wheels. It should be understood that it is also possible to supply each front wheel with a separately regulated brake pressure, and to supply the two rear wheels with a further regulated, common brake pressure.

RPM sensors 22–25 disposed on the wheels 2–5 furnish electrical signals, which are proportional to the applicable wheel rpm, to the evaluation circuit 20 over lines 26–29. From these wheel rpm signals, the rotational acceleration ω of the wheels, the speed $\dot{x}_A$ of the motor vehicle, and the wheel slip s are calculated. Details of the evaluations carried out in the evaluation circuit 20 will be described hereafter.

Based on these evaluations, output signals are generated by the evaluation circuit 20 and delivered via a bus 32 to the valve block 10. The valve block 10 thereupon supplies the brake pressure to the individual wheels 2–5 in such a way that the brake forces are transmitted wheel-selectively extremely effectively from the wheels to the road, and the motor vehicle remains stable, or it is stabilized if necessary, and it retains its steerability.

The drive and braking forces of a motor vehicle are transmitted by the frictional force $F_R$ between the circumferential surface of the tire of a wheel and the surface of the road. The frictional force is transmitted wheel-selectively and also as a function of the load acting upon the individual wheel. It can accordingly be calculated as follows:

$$F_R = \mu * F_Z \quad (1)$$

In this equation, $F_Z$ is the normal force acting vertically upon the road, which is equivalent to the portion of the vehicle mass that is supported by one wheel. The variable μ is the frictional value or the coefficient of friction, which depends essentially on the paving material, and on the structure and condition of the road. It varies over a wide range, for instance between dry asphalt pavement and a layer of wetting ice on the road. Where again it is determined wheel-selectively, i.e. separately for each wheel, since firstly it is known that motor vehicle wheels may be located at points on the road whose adhesion varies considerably, and secondly, the conditions of the treads of the various tires may differ from one another.

A frictional force can be built up only by means of a wheel slip s $$s = 1 - \frac{\omega r_R}{\dot{x}_A} \qquad (2)$$

which is defined as the relative difference between the vehicle speed $\dot{x}_A$ and the rotational wheel speed ω times the rolling radius $r_R$ of the wheel.

Figure 2:
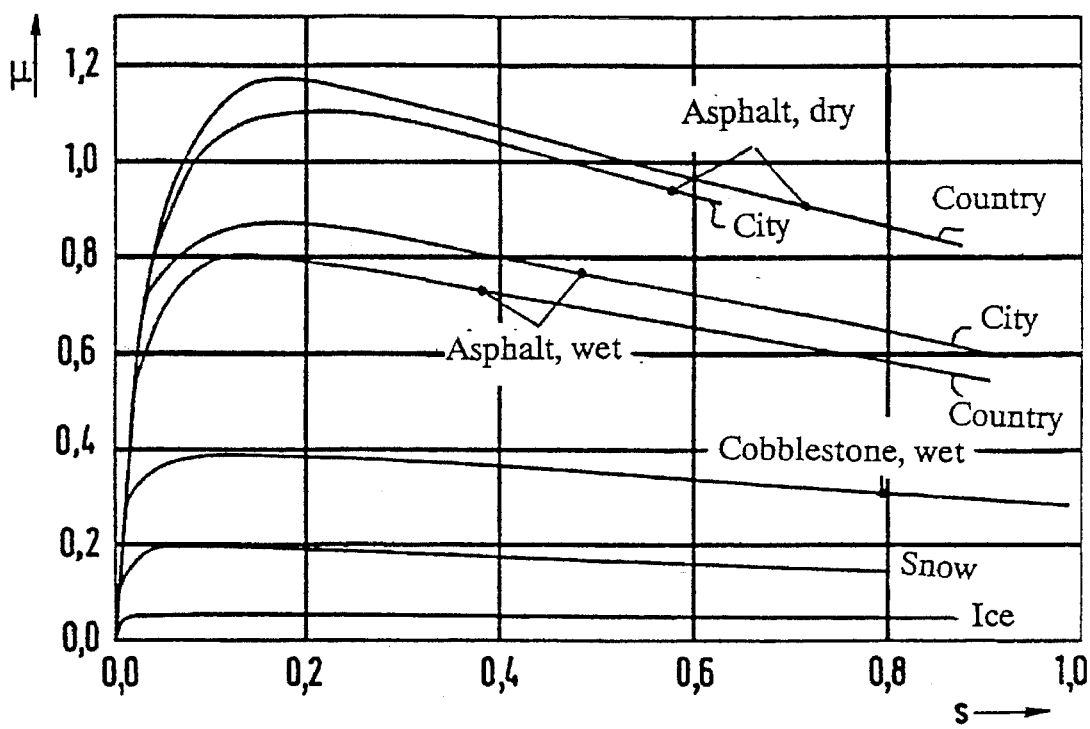
FIG. 2 is a diagram showing the coefficient of friction of various types of pavement as a function of slip.

Referring now to FIG. 2, measurements of the coefficient of friction μ(s) as a function of the wheel slip s for various road surfaces are known from the literature. All the curves shown in the graph begin at the point μ=0 for s=0 and then rise each to their respective maximum, which is at a wheel slip value of approximately s=0.005 ... 0.25. After that, the frictional value μ decreases, and a transition takes place from static friction, which is essential for force transmission, to kinetic or sliding friction.

With an anti-lock brake system, the stopping distance of a motor vehicle is shortened and at the same time its steerability is maintained. To that end, the rotational speed ω of the individual wheels is measured, and by differentiation the angular acceleration or deceleration of the wheel ω is calculated. With increasing brake pressure p, the wheel slip s increases, and the maximum frictional value μ(s) is exceeded. After the maximum, the sign (+or −) of the slope of the coefficient of friction curve changes, and this causes instability of the ABS control loop. Incipient locking of the wheel can be detected from a sharp rise in the wheel deceleration. A sharp rise in the wheel deceleration signals causes the ABS control unit to reduce the brake pressure p. If the wheel deceleration decreases after that, then the control unit raises the brake pressure again. The resultant cyclic changes in brake pressure have the effect that the frictional value is kept in the region of its maximum, so that short stopping distances are achieved.

On the other hand, the lateral guide forces at the wheels increase as the wheel slip increases, thus decreasing steerability. As an additional condition, the wheel slip is therefore limited to a maximum value of approximately s≦ 0.25. Prior art anti-lock brake systems are designed in accordance with empirical values. The determination described here of the friction characteristic μ=μ(s), or in other words the dependency of the coefficient of friction on the wheel slip, makes it possible—since it can be done in real time—to systematize the anti-lock control.

Figure 3:
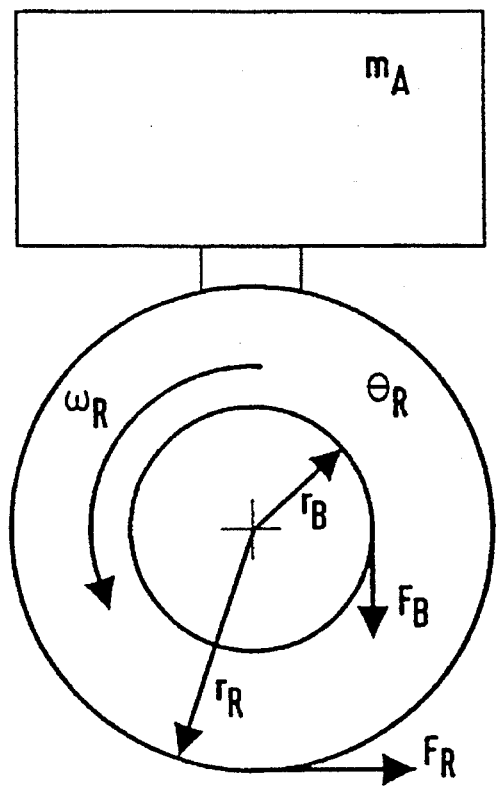
FIG. 3 is a diagrammatic view of a single-wheel model for determining the coefficient of friction according to the invention.

Referring now to FIG. 3, determining or estimating the frictional value or the coefficient of friction is based on a single-wheel model. In addition to the variables already mentioned, the figure also shows the following: the portion $m_A$ of the vehicle mass that is supported by this one wheel; the moment of mass inertia $\theta_R$ ($Theta_R$) of the wheel; the brake radius $r_B$; and the brake force $F_B$.

The frictional force $F_R$ slows down the vehicle speed as follows:

$$-m_A \ddot{x}_A = F_R, \qquad (3)$$

in which the difference between the braking torque and the torque of friction slows down the wheel rotation as follows:

$$\Theta_R \dot{\omega}_R = F_B \cdot r_B - F_R \cdot r_R \qquad (4)$$

The frictional force results from the following equation:

$$F_R = \mu(s) F_z = \mu(s) \cdot m_A \cdot g \qquad (5)$$

With a frictional value $\mu_B$ at the brake disk or brake shoe, the brake force can be expressed as follows:

$$F_B = \mu_B \cdot p_B \cdot A_B \qquad (6)$$

in which $p_B$ is the brake pressure, and $A_B$ is the effective pressure surface area of the brake pad on the brake disk or brake drum. The following system equations are thus obtained for the single-wheel model:

$$\ddot{x}_A(t) = -g \cdot \mu(s(t)), \qquad (7)$$

$$\dot{\omega}_R(t) = \frac{m_A \cdot g \cdot r_R}{\Theta_R} \mu(s(t)) - \frac{\mu_B A_B r_B}{\Theta_R} p_B(t)$$

The wheel speeds are typically measured by successive inductive scanned values. The time intervals between the scanned values vary with the rotational speed. For the sake of simplicity, a constant scanning time $T_A$=10 ms is chosen here. This produces the following discrete description of the single-wheel model:

$$\frac{\omega_R(n) - \omega_R(n-1)}{T_A} + \frac{\mu_B A_B r_B}{\Theta_R} p_B(n) = \frac{m_A g r_R}{\Theta_R} \mu(n) \qquad (8)$$

The rotational speed of the wheel $\omega_R$ (n) and the brake pressure $p_B$ (n) are measured continuously. Here, n is the counting index for the successive measurements. The actual frictional value μ(n) is determined with a recursive estimation algorithm by means of the recursive least squares estimation method—described in the literature as the RLS method. With a measurement variable y(n)

$$y(n) = \frac{\omega_R(n) - \omega_R(n-1)}{T_A} + \frac{\mu_B A_B r_B}{\Theta_R} p_B(n) \qquad (9)$$

and a vehicle parameter X $$X = \frac{m_A g r_R}{\Theta_R} \qquad (10)$$

the following recursive estimation algorithm results:

$$\hat{\mu}(n) = \hat{\mu}(n-1) + k(n)(y(n) - X^* \hat{\mu}(n-1)) \qquad (11)$$

with an error feedback amplification factor k(n)

$$k(n) = \frac{1}{1 + X^2 P(n-1)} X * P(n-1), \qquad (12)$$

in which P(n−1) is the covariance of the estimation error, $$P(n-1) = 10^{q} * (y(n-1) - X^* \hat{\mu}(n-1))^{-2} \cdot \qquad (13)$$

In this equation, q is a predetermined number, which can for instance assume the values q=2, 3 ... 8.

Figure 4:
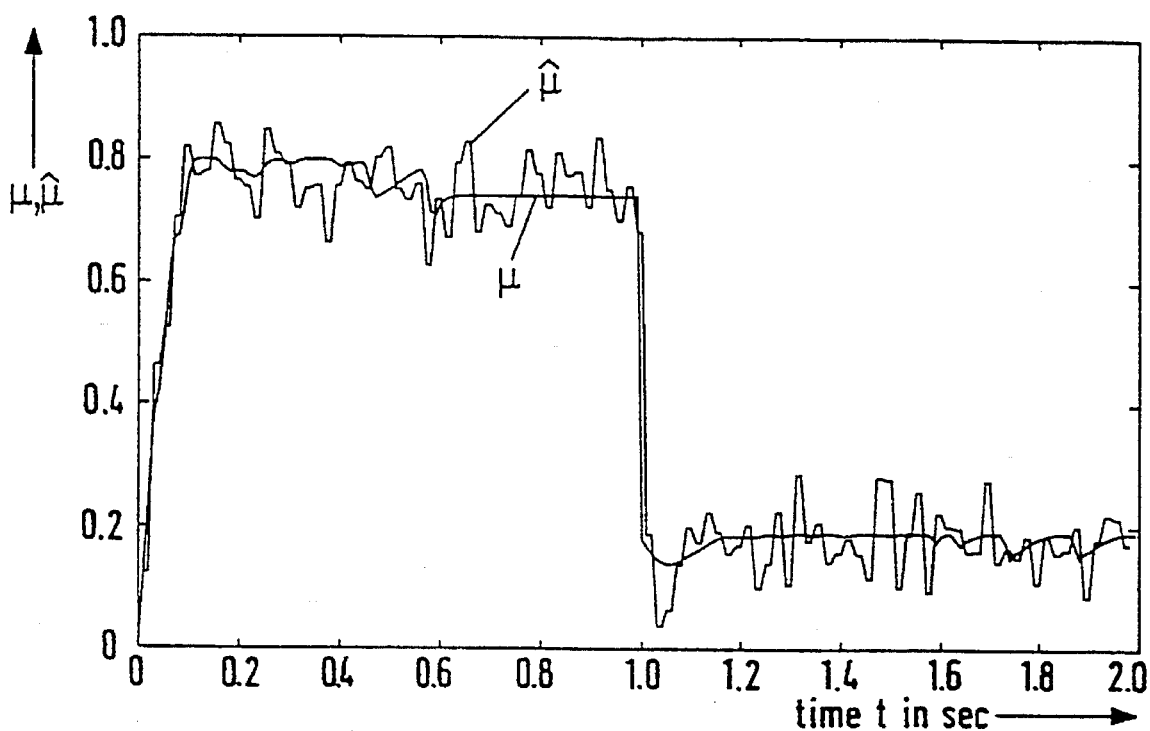
FIG. 4 is a graph showing the course over time of a coefficient of friction ascertained according to the invention.

Referring now to the graph of FIG. 4, it can be seen that the estimated value $\hat{\mu}$ of the frictional value determined with the above algorithm correlates very well with a predetermined frictional value μ, which approximately at time t=1s drops abruptly, so that it is approximately equivalent to the transition from a dry asphalt pavement to an iced-over road surface.

For effective ABS regulation, it is necessary to know frictional value or coefficient of friction as a function of the wheel slip, i.e. the friction characteristic. The literature has proposed the following function for this dependency:

$$\mu(s) = C_1(1 - e^{c_2 s}) - c_3 s \tag{14}$$

However, it is a grave disadvantage that it results in non-linear estimation algorithms. An approximation equation is therefore used herein:

$$\mu(s) = As + B\sqrt{s}, \tag{15}$$

which produces the following linear estimation algorithm:

$$\hat{\mu}(n) = As(n) + B\sqrt{s(n)}, \tag{16}$$

in which A and B are parameters of a curve with which the coefficient of friction to be determined is approximated. They are derived from the curve parameters A and B, represented as a vector $$b^T = [AB]$$

from the measured values of the wheel slip s represented as a data vector $$\underline{X}^T = [s\sqrt{s}]$$

and from the coefficient of friction $\hat{\mu}(n)$ ascertained as described above. A prediction value for the friction characteristic is calculated with the following equations:

$$\mu(n) = X^T(n) \cdot b(n)$$

$$\hat{b}(n) = b(n-1) + k(n)(\mu(n) - X^T(n)\hat{b}(n-1),$$

$$k(n) = P(n-1)X(n)(1 + X^T(n)P(n-1)X(n))^{-1}$$

An estimation value $\mu(n)$ for the prediction at the time n is ascertained from the results of a measurement at time n−1. A new estimated value $\hat{b}(n)$ at the time n is correspondingly calculated from the estimated value at the time n−1. A vector k(n) at time n is likewise calculated from the values at the time n−1. In the literature, this vector is also called the Kalman amplification factor. The covariance matrix P(n−1) contained in it, is calculated with the equation $$P(n) = 10^{q} \cdot |\mu(n) - X^T(n)\hat{b}(n)|^2 \cdot I \tag{18}$$

but with the scanned values at time n−1. It depends on the estimated error. I here is the unit matrix.

Figure 5:
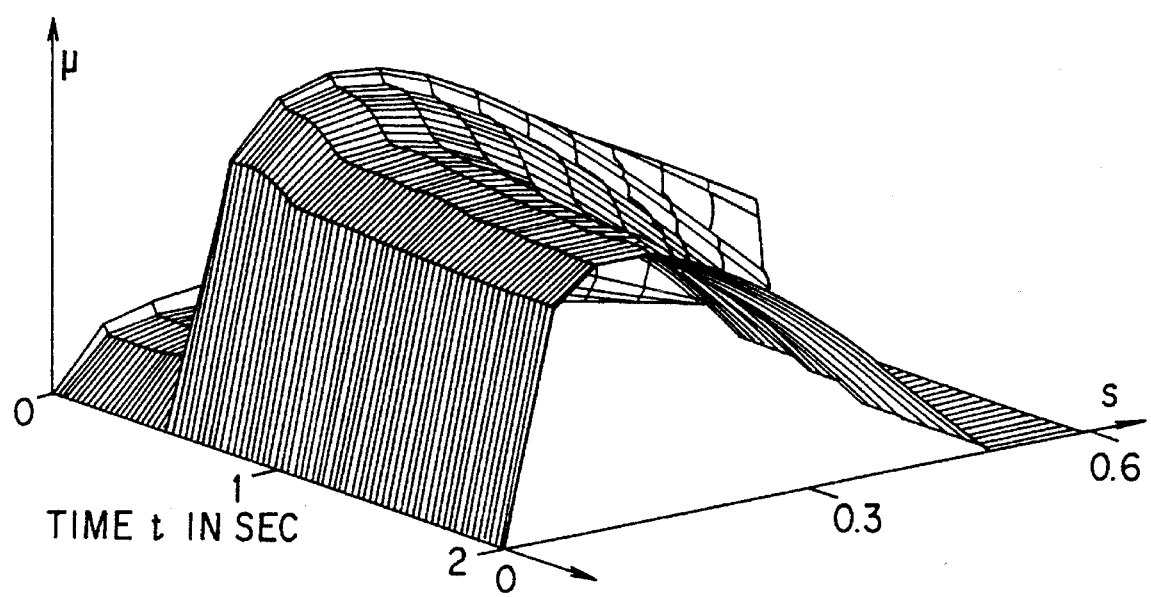
FIG. 5 is a three-dimensional graph of frictional characteristic, ascertained according to the invention, as a function of time and slip.

The model upon which the calculation is based herein in accordance with equation (15) leads to good results—as can also be seen from the diagram of FIG. 5—if restrictions as to the location of the curve maximum are allowed. The greater deviations after the maximum are tolerable, since modern ABS systems do not operate in that range.

A model, preferable selectively used here, of the friction characteristic $$\mu(s) = \frac{s}{A + Bs + Cs^2} \tag{19}$$

employs three parameters A, B and C, which provide a good approximation for the frictional value over the entire wheel slip range. The initial slope of the curve $\mu(s)$ is $$\mu(0) = 1/A \tag{20}$$

and the maximum of the frictional value is $$\mu_{max} = \mu(s_0) = \frac{\sqrt{A/C}}{(2A + B\sqrt{A/C})}, \tag{21}$$

at a wheel slip value $s_O$ $$s_0 = \sqrt{A/C}. \tag{22}$$

A model of the friction characteristic in accordance with a relationship $$y(s) = \frac{s}{\mu(s)} = A + Bs + Cs^2 \tag{23}$$

likewise results in a linear estimation algorithm.

The estimation algorithm described minimizes the error square of the estimation error. It is advantageous that all the previously measured values enter into the actual estimation, so that more information is available for the estimation. As a result, errors in estimating the wheel contact force are better compensated for than with previously known methods.

We claim:

1. A method for determined a frictional value between a motor vehicle tire and a road surface, which comprises:
    ascertaining values of vehicle speed, angular acceleration of a vehicle wheel, and brake pressure;
    calculating a wheel slip from the values;
    approximating a dependency of a coefficient of friction between a road surface and a vehicle tire from the wheel slip with a non-linear approximately equation;
    estimating a current estimation value for the coefficient of friction with a recursive estimation algorithm from measurement values previously ascertained during a preceding measuring instant; and
    determining a frictional value between the motor vehicle tire and the road surface from the coefficient of friction estimated with the recursive estimation algorithm.

2. The method according to claim 1, which further comprises approximating the coefficient of friction in the approximating step with the equation $\mu(s) = As + B\sqrt{s}$, wherein A and B are parameters for the approximation, $\mu$ is the coefficient of friction, and s is the wheel slip.

3. The method according to claim 1, which further comprises approximating the coefficient of friction in the approximating step with the equation $$\mu(s) = \frac{s}{A + Bs + Cs^2},$$

wherein A, B and C are parameters for the approximation, $\mu$ is the coefficient of friction, and s is the wheel slip.

4. The method according to claim 1, which further comprises estimating, in the estimating step, the coefficient of friction $\mu$ with the following recursive estimation algorithm:

$$\hat{\mu}(n) = \hat{\mu}(n-1) + k(n)(y(n) - X^* \hat{\mu}(n-1)),$$

in which $$y(n) = \frac{\omega_R(n) - \omega_R(n-1)}{T_A} + \frac{\mu_B A_B r_B}{\Theta_R} p_B(n)$$

is a variable formed from the measured values, $\omega_R$ is an angular speed of the respective wheel, and n is a dummy index of consecutive measurement instants;

$$X = \frac{m_A g r_R}{\Theta_R}$$

is a vehicle parameter, $m_A$ is a portion of a vehicle mass on the respective wheel, $r_R$ is a rolling radius of the wheel, and $\Theta_R$ is a mass moment of inertia of the wheel;

$$k(n) = \frac{1}{1 + X^2 P(n-1)} X * P(n-1)$$

is an amplification factor for error feedback; and $P(n-1) = 10^{q*}(y(n-1) - X* \hat{\mu}(n-1))^2$ is a covariance of an estimation error at a measurement time $n-1$;

5. The method according to claim 1, which further comprises determining the coefficient of friction as a function of a wheel slip with a recursive estimation algorithm.

6. The method according to claim 5, which further comprises determining the coefficient of friction on the basis of a model $$\mu(s) = As + B\sqrt{s}$$

in which A and B are curve parameters with a vector representation $b^T = [AB]$ calculated from the measured wheel slip values with the vector representation $X^T = [s\sqrt{s}]$ and from a previously ascertained coefficient of friction $\mu(n-1)$, and determining a current coefficient of friction $\mu(n)$ with the following estimation algorithm:

$$\mu(n) = X^T(n)*b(n)$$

in which $$\hat{b}(n) = b(n-1) + k(n-1)(\mu(n) - X^T(n)\hat{b}(n-1))$$

$$k(n) = P(n-1)X(n)(1 + X^T(n)P(n-1)X(n))^{-1}$$

$$P(n-1) = 10^{q*}|\mu(n-1) - X^T(n-1)\hat{b}(n-1)|^{2*}I$$

and I is a unit matrix.

7. The method according to claim 1, which further comprises determining the coefficient of friction $\mu(s)$ on the basis of a model $$\mu(s) = \frac{s}{A + Bs + Cs^2}$$

wherein A, B, and C are parameters for the approximation, and s is the wheel slip.

8. The method according to claim 5, which further comprises transmitting the frictional value determined in the determining step to an anti-lock brake system or a traction control system.

9. A circuit configuration for determining a coefficient of friction between a motor vehicle tire and a road surface, comprising:

a plurality of sensors disposed at a motor vehicle for continuously measuring an angular speed of a wheel and a braking pressure at a wheel;

an evaluation circuit connected to said sensors and receiving the signals from the sensors, said evaluation circuit being programmed to calculate and angular acceleration from the angular speed measured by a respective one of said sensors; and to evaluate a coefficient of friction between a motor vehicle tire and a road surface from the angular acceleration and from the braking pressure with a recursive estimation algorithm.

10. The circuit configuration according to claim 9, which further comprises means for connecting an output of said evaluation circuit to an anti-lock brake system.

11. The circuit configuration according to claim 9, which further comprises means for connecting an output of said evaluation circuit to a traction control system.

12. In an anti-lock brake system or a traction control system in which a coefficient of friction between a motor vehicle tire and a road surface is utilized as a control parameter, an improved circuit configuration for determining the coefficient of friction between the motor vehicle tire and the road surface, the improvement which comprises:

a plurality of sensors disposed at the motor vehicle for continuously measuring a vehicle travel speed, an angular speed of a wheel, and a braking pressure at a wheel;

an evaluation circuit connected to said sensor and receiving the signals from said sensors, the evaluation circuit being programmed for calculating an angular acceleration from the angular speed measured by a respective one of said sensors;

for calculating a wheel slip from the vehicle travel speed and from the angular acceleration;

for approximately a dependency of the coefficient of friction between the tire and the road surface from the wheel slip with a non-linear approximation equation; and for determining a current estimated value of the coefficient of friction between the motor vehicle tire and the road surface from measurement values ascertained in an immediately preceding instant with a recursive estimation algorithm.

* * * * *